United States Patent [19]
Freed

[11] Patent Number: 6,035,258
[45] Date of Patent: Mar. 7, 2000

[54] METHOD FOR CORRECTION OF QUANTITATIVE DNA MEASUREMENTS IN A TISSUE SECTION

[76] Inventor: Jeffrey A. Freed, 204 2nd St., SW., Puyallup, Wash. 98371

[21] Appl. No.: 08/929,273

[22] Filed: Sep. 12, 1997

[51] Int. Cl.[7] .................................................. G06G 7/48
[52] U.S. Cl. ................................ 702/20; 702/20; 702/27; 395/500.32
[58] Field of Search ................................ 702/20, 19, 23, 702/27; 356/39; 382/133; 395/500.32

[56] References Cited

U.S. PATENT DOCUMENTS 5,235,522  8/1993  Bacus ........................................ 364/497

OTHER PUBLICATIONS

Bacus JW and Bacus JV. A method of correcting DNA ploidy measurements in tissue sections. Modern Pathology 7:652–664, 1994.

McCready RW and Papadimitrious JM. An analysis of DNA cytomorphometry on tissue sections in a rat liver model. Analytical and Quantitative Cytology 5:117–123, 1983.

Bins M, Takens F. A method to estimate the DNA content of whole nuclei from measurements made on thin tissue sections. Cytometry 6:234–237, 1985.

Rigaut JP, PersozA. The 'corpuscle' stereological problem—re–evaluation using slab fragment volumes and applications to the correction of DNA histograms from sections of spherical nuclei. Journal of Microscopy 156: 371–382, 1989.

Haroske G, MeyerW, DimmerV,et al. Feasibility and limitations of a cytometric DNA ploidy analysis procedure in tissue sections. Zentralblatt für Pathologie 139 : 407–417, 1993.

Freed JA. Possibility of correcting image cytometric nuclear DNA (ploidy) measurements in tissue sections. Insights from computed corpuscle sectioning and the reference curve method. Analytical and Quantitative Cytology and Histology 19:376–386, 1997.

*Primary Examiner*—Marc S. Hoff
*Assistant Examiner*—Hien Vo

[57] ABSTRACT

The operator downloads, from a data file into the random access memory of a personal computer, integrated optical density and profile area data for a plurality of nuclei and partial nuclei in a Feulgen-stained histologic tissue section; the thickness of the section; and the integrated optical density of an intact diploid nucleus. The operator then operates a computer program which plots the data curve together with a reference line and a reference curve. The data curve is scaled and the reference curve is recalculated and redrawn through a number of iterations until the operator is satisfied that the scaled data curve terminates on the reference line, and the scaled data curve is as nearly congruent as possible with the latest reference curve. The program calculates and displays the corrected DNA index on a video screen, the contents of which the operator may print on a printer.

10 Claims, 6 Drawing Sheets

Integrated Optical Density

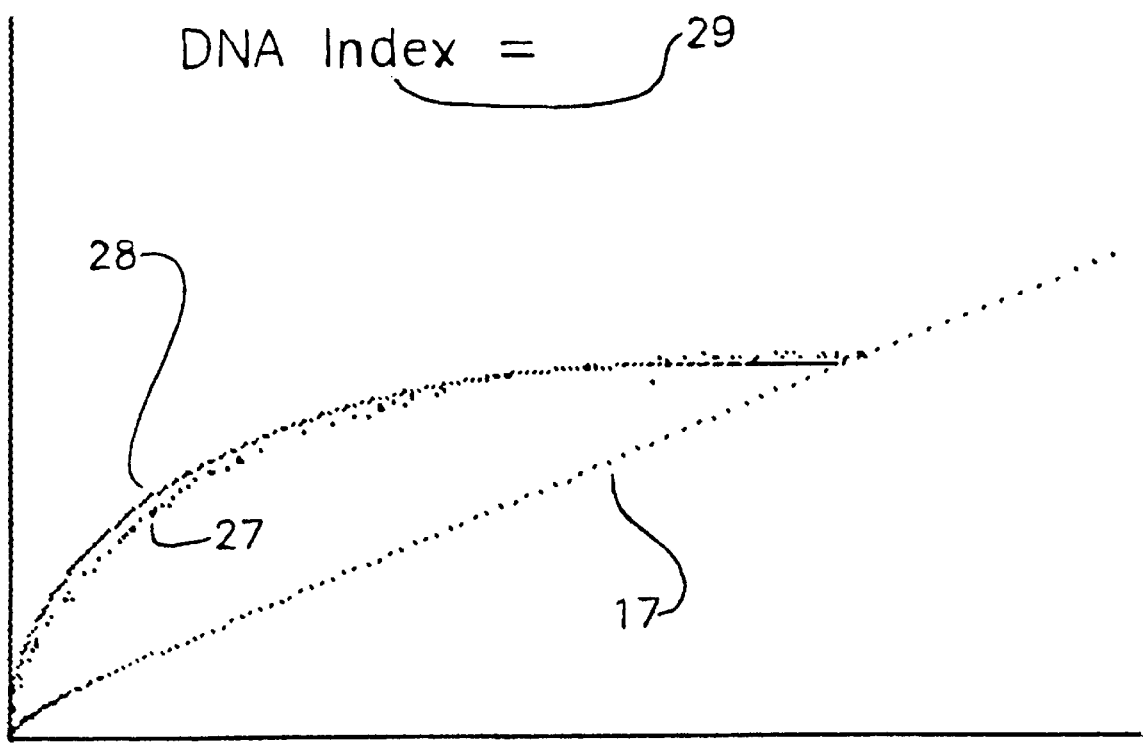

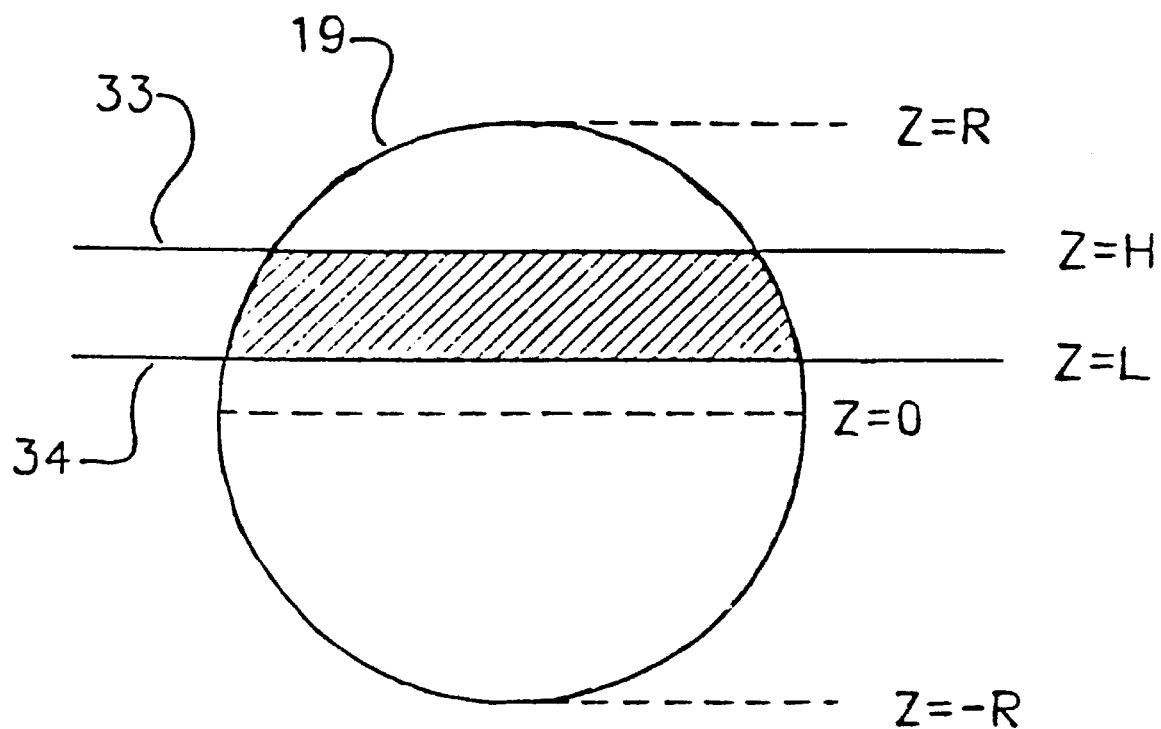

METHOD FOR CORRECTION OF QUANTITATIVE DNA MEASUREMENTS IN A TISSUE SECTION

CROSS-REFERENCES TO RELATED APPLICATIONS

This invention, in some of its embodiments, uses U.S. Pat. No. 5,918,038 to Freed for General Method for Determining the Volume and Profile Area of a Sectioned Corpuscle.

BACKGROUND

1. Field of Invention

This invention relates to the interpretation of data from an assay of a biological cell sample, and more particularly, to correction of DNA quantitative measurements in a tissue section.

2. Description of Prior Art

Cancer diagnosis and prognosis is largely dependent on the pathologic examination of tissue surgically removed from a patient. The specific diagnosis is made by a pathologist, who classifies the tumor by site and by cell of origin after examining stained histologic sections of the fixed, paraffin-embedded cancer tissue. The prognosis depends on many factors, including the specific diagnosis, the presence and pattern of tumor metastasis, the extent of tumor at its site of origin and its proximity to vital structures, and the tumor grade as assessed by a pathologist. In some organs, such as the prostate, the usual determinants of prognosis are inadequate to provide a patient-specific prognosis, especially when such is desired prior to definitive therapy. Consequently, other prognostic indicators have been sought.

One prognostic indicator which has been valuable in the cancers of certain organs is DNA ploidy, which is the ratio of the quantity of DNA in a cancer cell to that in a normal cell in the resting phase of its growth cycle. In general, tumors with normal resting-phase cellular DNA content (diploid) have a better prognosis than those with twice that amount (tetraploid), and these in turn have a better prognosis than those with abnormal DNA content which is not tetraploid (aneuploid).

The cellular DNA is located in the nucleus. Various methods have been developed for measuring the DNA content of whole nuclei. These methods do not make it possible for the measured cells to be correlated with their position or appearance in a standard histologic section. Thus, it is likely that normal cells will be measured together with tumor cells. Also, distinct areas of tumor cannot be measured separately. An even more important consideration is that very small samples, such as prostate thin core biopsies, are unsuitable.

All of these limitations have been overcome by measuring the DNA content of nuclei and partial nuclei in Feulgen-stained standard histologic sections. A new problem is created, however, by the inevitable inclusion of partial nuclei among the analyzed nuclei. In many sections, because the nuclear diameter exceeds the section thickness, all of the nuclei in the section will be partial. In U.S. Pat. No. 5,235,522 to Bacus for Method and Apparatus for Automated Analysis of Biological Specimens, an apparatus and method for measuring the DNA content of nuclei in tissue sections is described, as well as a method for correction of DNA measurements necessitated by the analysis of partial nuclei. Bacus and Bacus also have described this method of correcting DNA measurements in A Method of Correcting DNA Ploidy Measurements in Tissue Sections, published in Modern Pathology, Vol. 7, pp. 652–664, 1994. The Bacus correction makes three assumptions: 1) all nuclei are spherical, 2) all nuclei have a homogenous intranuclear DNA distribution, and 3) all nuclei with a profile area greater than $\pi T^2/4$, where T is the section thickness, have been sectioned such that the center of the nucleus lies midway between the top and bottom of the tissue section. In an actual tissue section, the nuclei deviate from perfect spheres, the DNA distribution may not be homogeneous, and the nuclei are sectioned at essentially random positions and orientations. It is clear that the Bacus correction undercorrects most of the measurements, and would overcorrect some of the measurements, such as those made on a central section of an ellipsoidal nucleus aligned with the plane of the section, or those made on a centrally-sectioned nucleus in which most of the DNA is concentrated centrally. The Bacus method creates a histogram (FIG. 1) from the corrected DNA measurements, which shows a large number of bars 1 to the left of the bar representing the true whole-nucleus DNA content 2. These bars 1 represent partial nuclei for which the Bacus correction was insufficient, but may also be interpreted or misinterpreted as subpopulations of cells with different DNA content, or as cells at different points in the cell cycle. In many cases, such a misinterpretation might result in the classification of a prognostically favorable tumor as unfavorable. In cases of undercorrection or overcorrection of the modal DNA quantity, a tumor might be considered more or less prognostically favorable than would be inferred from its true ploidy. Also, histograms of quantitative DNA measurements in whole-nucleus preparations show very discreet peaks, reflecting discreet ploidy values of the measured nuclei; but when partial nuclei are measured, whether or not the measurements are corrected, the peaks are very blurred and may not be distinguishable as such (FIG. 1). The Bacus method allows the operator to define classes of attributes, thereby excluding many unwanted partial nuclei from analysis; such an approach is helpful but may be of limited value because the a priori classes may not accord with the natural classes in the specimen being analyzed.

OBJECTS AND ADVANTAGES

Several objects and advantages of the present invention are:

(a) to provide a method which demonstrates the relationship of all the partial nuclei in a tissue section to the corresponding intact nuclei which existed prior to sectioning;

(b) to provide a method to more accurately classify tumors into the correct prognostic categories;

(c) to provide a method which more readily distinguishes tumor cell subpopulations of different ploidy in a mixed sample;

(d) to provide a method in which data sets that are not amenable to correction can be distinguished from those that are amenable to correction;

(e) to provide a method in which randomly oriented, randomly positioned, non-spherical nuclei can be more readily analyzed;

(f) to provide a method which is not dependent on the limiting and incorrect assumptions upon which the prior art is based; and (g) to obviate the need for assignment of the nuclei and partial nuclei in a tissue section to different a priori classes.

DRAWING FIGURES

FIG. 5 is a representation of the final video screen after the reference curve has been recalculated and redrawn to coincide as closely as possible with the horizontally-scaled data curve; and FIG. 6 is a representation of a reference sphere.

Figure 1:
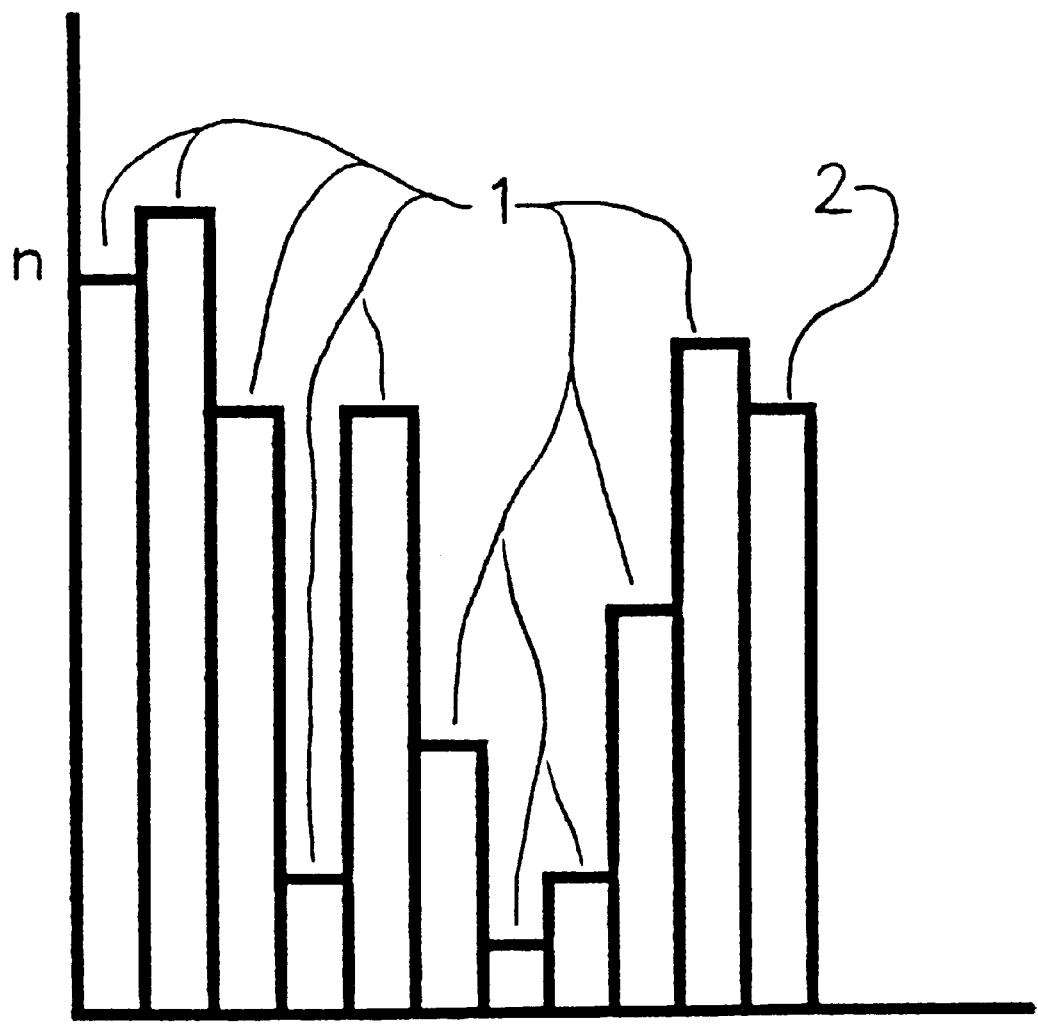
FIG. 1 is a histogram shown to illustrate some limitations of the prior art.

REFERENCE NUMERALS IN DRAWINGS 1 histogram bars corresponding to partial nuclei
2 histogram bar corresponding to true whole-nucleus DNA content
13 start program
14 download data
15 display first video screen
16 data curve
17 reference line
18 reference curve
19 reference sphere
20 operator prompt
21 operator decides to quit program
22 program halts
23 operator prompt
24 operator prompt
25 program calculates F and $V_i$
26 screen display is redrawn
27 horizontally-scaled data curve
28 redrawn reference curve
29 statement displayed preceeding program output
30 print screen display
31 operator causes program to loop
32 program loops
33 top sectioning plane
34 bottom sectioning plane
35 first control point

SUMMARY

In accordance with the present invention, a process for correcting quantitative DNA measurements in tissues sections comprises a computer program in which the measured data are compared to a sequence of reference curves until a best-fit reference curve is found. The known attributes of this best-fit reference curve enable the calculation of the corrected DNA index.

DESCRIPTION AND OPERATION— PREFERRED EMBODIMENT

Figure 2:
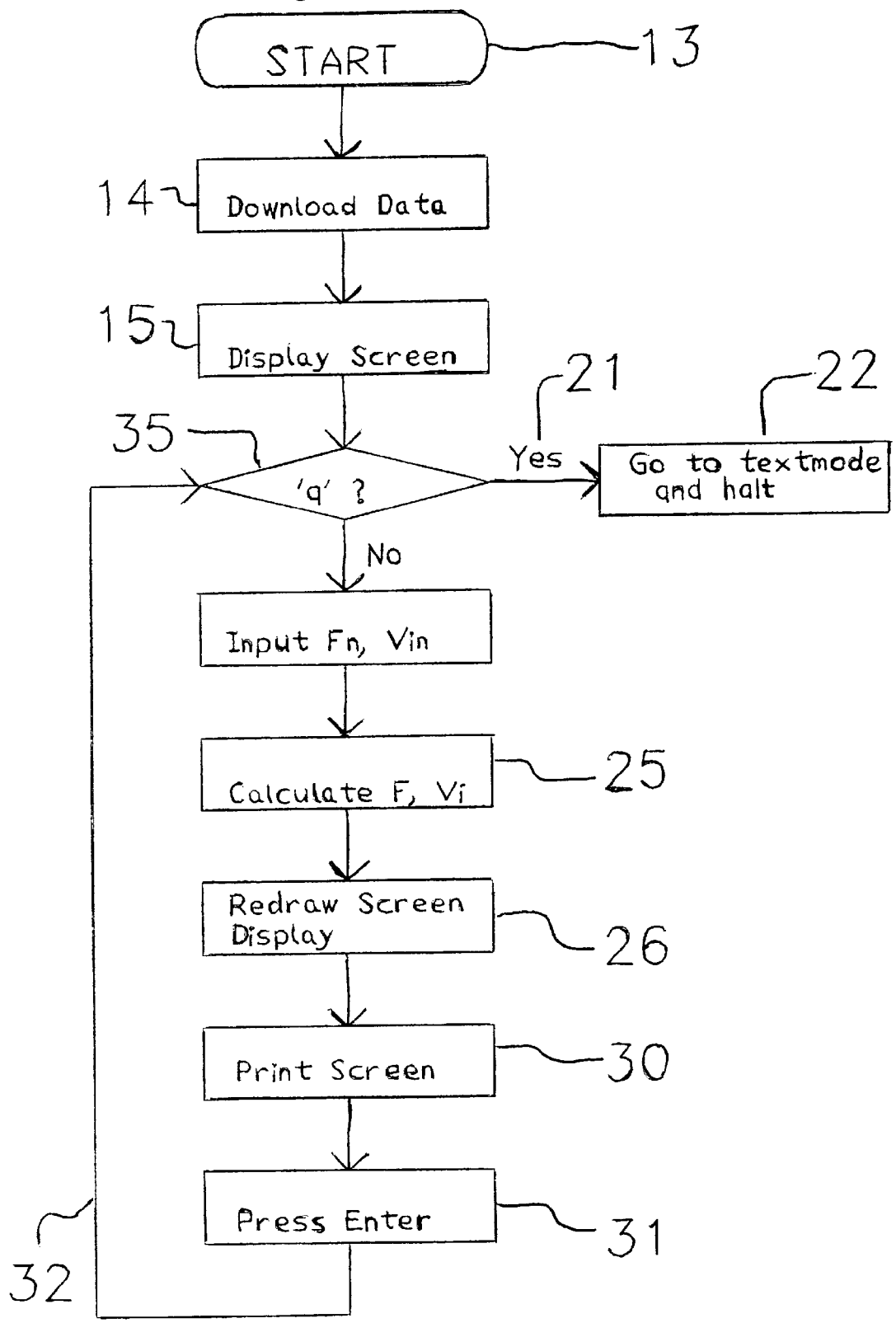
FIG. 2 is a flow diagram of the overall process of correcting DNA quantitative measurements in a tissue section.
Figure 3:
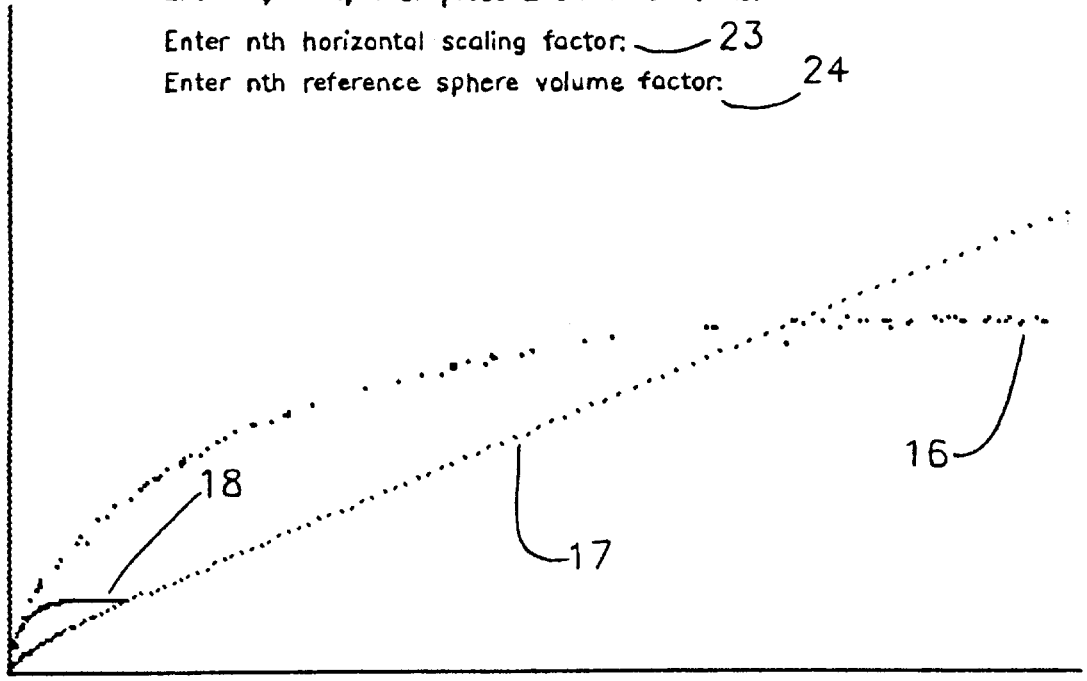
FIG. 3 is a representation of the first video screen which appears after the data has been downloaded.

In the preferred embodiment, a computer program written in TurboPascal v. 2.0 (Borland International, Inc., Scotts Valley, Calif.) runs on an IBM-compatible personal computer equipped with central processing unit, random access memory, a floppy disk drive, a hard drive, a standard keyboard, a printer, and a video monitor. FIG. 2 shows a flow chart of the program logic. When the program is started 13, the video screen prompts the operator for the name of the data file. The user enters the file name using the keyboard. The program then finds the data file and downloads 14 the data from the file, which resides on either a floppy disk or on the hard drive, into random access memory. The data file contains the following data: The file size, the nuclear profile area ($A_s$) and integrated optical density data ($D_s$) for a plurality of nuclei and partial nuclei in a Feulgen-stained histologic tissue section, the thickness of the tissue section, and the integrated optical density of an intact diploid nucleus. When data acquisition is complete, the program switches the video display to graphics mode and displays 15 the first screen (shown in detail in FIG. 3), in which the data curve 16 $[(D_{s1}, A_{s1}/A_t), (D_{s2}, A_{s2}/A_t) \ldots (D_{sn}, A_{sn}/A_t)]$ (where $A_t=\pi T^2/4$) is plotted, suitably scaled so that all points fit on the screen of the video monitor. A reference line 17, and a reference curve 18 derived from a reference sphere 19 the diameter of which equals the section thickness, are displayed on the same screen (FIG. 3). The statement 20, "Enter 'q' to quit or press Enter to continue", is displayed at the top of the screen. This is the first control point 35. If the operator presses the q key and then the Enter key 21, the program returns the video display to text mode and halts 22. If the operator presses only the enter key, the statement 23, "Enter nth horizontal scaling factor:", is displayed on the next line. The operator enters a real number value using the keyboard. The entered value is assigned to the data array $[F_1 \ldots F_n]$ according to the round (n). Then the statement 24, "Enter nth reference sphere volume factor:", is displayed on the next line. The operator enters a real number value using the keyboard. The entered value is assigned to the data array $[V_1 \ldots V_n]$ according to the round (n).

Figure 4:
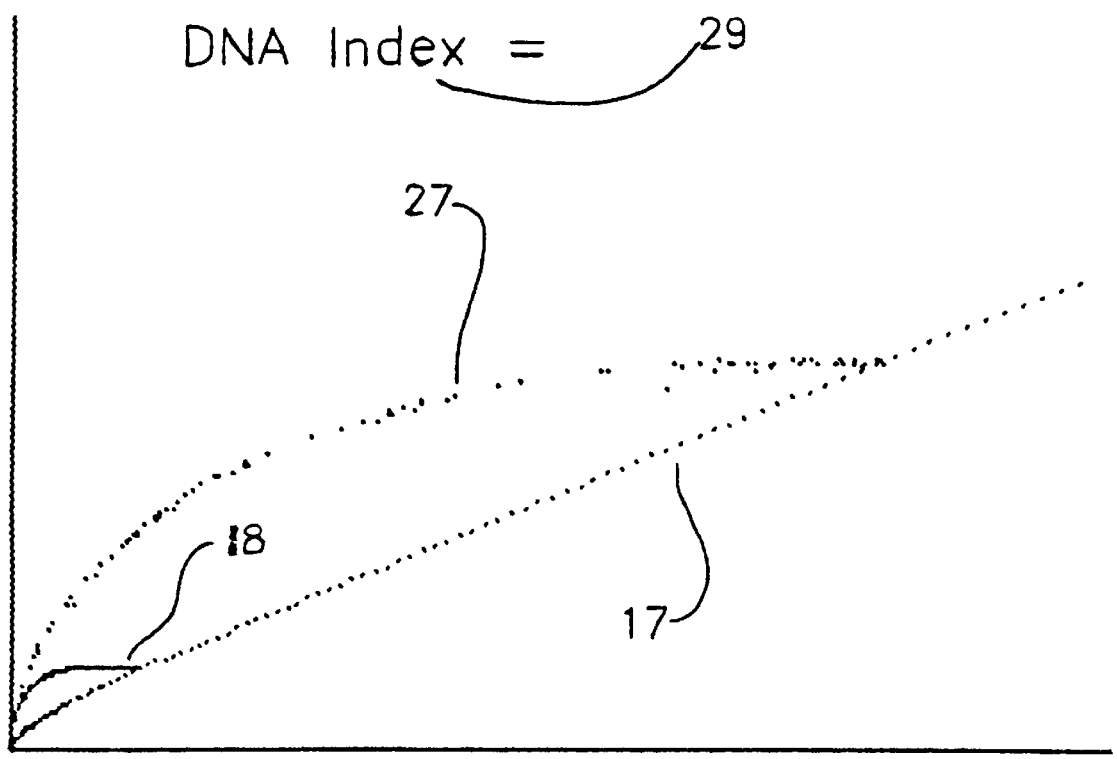
FIG. 4 is a representation of the video screen after the data curve has been horizontally scaled to terminate on the reference line.

The horizontal scaling factor, F and the reference sphere volume, $V_i$ are then calculated 25. The video screen display (FIG. 3) is then erased and redrawn 26 (FIG. 4) showing the now horizontally scaled data curve 27 terminating o n the reference line 17, and the reference curve 18. Also displayed at the top of the screen is the statement 29, "DNA Index=", followed by the calculated DNA index. (This number will not become meaningful until the end of this process.) The operator may now print the screen display 30 (by pressing the Shift and Print Screen keys together; initialization is required using the graphics command in DOS before the program is started). The operator now presses 31 the Enter key and the program loops 32 to the first control point 35 and another round begins.

After each round (see FIG. 5), the operator visually assesses the proximity of the terminus of the horizontally-scaled data curve 27 to the reference line 17 (always striving for a closer approximation), and the congruence of the redrawn reference curve 28 to the horizontally-scaled data curve 27 (always striving for the closest approximation to congruence). When the operator is satisfied, she may print the screen display 30. The value shown for the DNA index is now correct.

The reference line 17 is defined as $y=(2x+1)/3$ for $x>1$ and $y=x^{2/3}$ for $0<x\leq 1$; all possible reference curves 18, 28 terminate on the reference line 17.

A reference curve 18, 28 is a plot of volume ($V_s$) versus profile area ($A_s$) for a representative series of sections of a reference sphere 19 of radius R (refer to FIG. 6), where the volume of the intact reference sphere ($V_t$) and the section thickness (T) are given. Let z=H be the equation of the top sectioning plane 33, z=L be the equation of the bottom sectioning plane 34, and Q be H or L, whichever has the smaller absolute value. (In this example, Q=L.) L=H−T. H is allowed to vary from −R to R+T in 400 equal increments; for each step, $V_s$ is calculated according to the equation $V_s=\pi((R^2H-H^3/3)-(R^2L[|m]-L^3/3))$, and A, is calculated according to the equation $A_s=\pi(R^2-Q^2)$. A set of 400 points $[(V_{s1}/V_t, A_{s1}/A_t), (V_{s2}/V_t, A_{s2}/A_t) \ldots (V_{sn}/V_t, A_{sn}/A_t)]$ (where $V_t=\pi T^3/6$ and $A_t=\pi T^2/4$) is plotted and appears as the reference curve 18, 28 on the screen.

The horizontal scaling factor (F) is the product of the last-entered value Fn and all values entered on previous rounds ($F_1 \ldots F_n$). Thus, $F=\Pi^{Fn}$. In each round, after the last horizontal scaling factor ($F_n$) is entered, F is recalculated and the horizontally scaled data curve 27 [($D_{s1}F,A_{s1}/A_t$), ($D_{s2F}, A_{s2}/A_t$) ... ($D_{sn}F,A_{sn}/A_t$)] is displayed. Similarly, the volume of the intact reference sphere 19, $V_i$, is the product of the last-entered value ($V_{in}$) and all values entered on previous rounds; thus, $V_i=\Pi_{vil}^{vin}$. In each round, the reference curve 28 is redrawn based on the last calculated $V_i$. The DNA index (DI) is calculated as DI=$V_i$/FD, where D is the integrated optical density of an intact diploid nucleus, the value of which was downloaded from the data file.

The source code is included at the end of the specification.

SUMMARY, RAMIFICATIONS, AND SCOPE

Accordingly, the reader will see that the method of this invention can be used to obtain a corrected DNA index from the measurable attributes of cell nuclei in a tissue section. The display of the data as a curve is visually appealing and has the explanatory power, lacking in histogram-based methods, of relating all the partial nuclei, whose data points lie on the data curve, to the corresponding nuclei which existed prior to sectioning. Thus, a data curve illustrates all the nuclear sections obtained from a population of nuclei sharing the same ploidy. If two or more data curves appear on the same screen display, this indicates the existence of the corresponding number of distinct nuclear subpopulations of different ploidy, which can be analyzed, each in its turn, by the method of the present invention. Discrimination of subpopulations is much more difficult in histogram-based methods, because the histogram does not relate the partial nuclei to the corresponding nuclei which existed prior to sectioning, as the method of the present invention does. A related advantage of the present invention is that it avoids the error of treating every sectioned nucleus as a centrally-sectioned sphere. The present invention can be used in conjunction with synthetic data generated by U.S. Pat. No. 5,918,038 to Freed for General Method for Determining the Volume and Profile Area of a Sectioned Corpuscle, giving the operator the opportunity to become acquainted with the problems introduced by deviations from nuclear sphericity. In this fashion, the operator will learn how to judge the appropriateness or inappropriateness, in individual cases, of attempting to correct quantitative DNA measurements in a particular tissue section. Certain limiting assumptions of prior methods were avoided in the present invention, which would be expected to result in more accurate classification of tumors into prognostic categories in some cases.

Although the description above contains many specificities, these should not be construed as limiting the scope of the invention but as merely providing an illustration of the presently preferred embodiment of this invention. Thus, data could be entered from a keyboard rather than downloaded from a file. Also, many specific details of the video screen displays and the program logic could be rendered differently without altering the result. For example, the choice of plotting $D_s$ on the abscissa and $A_s/A_t$ on the ordinate is arbitrary, these assignments could be reversed. Also, the reference line is very convenient but is not required.

Thus the scope of the invention should be determined by the appended claims and their legal equivalents, rather than by the example given.

```
PROGRAM RCM;

const
xscreen: integer=320;
yscreen: integer=200;
pi: real=3.141593;
type
template=array[1..100]of real;
var
arya,aryb,naryb: template;
bnfile: file of real;
fname,fname2: string[15];
datamt,i,ic,color1,colr,sggn: integer;
dat,vri,y,dipdna,newthk,thkness,factorx,factory,maxarea,maxdna: real;
increment,q1,q0,a,b,ploidy,modcrc,right,top,bottom,left,modif: real;
ch,ch1,ch2: char;
Procedure setpt(xu,yu,rt,lt,tp,bm: real);
var
xs,ys: real;
begin
xs:=(xu-lt)*xscreen/(rt-lt);
ys:=200-(yu-bm)*yscreen/(tp-bm);
plot(trunc(xs),trunc(ys),colr);
end;
Procedure readdata;
begin
maxdna:=0; maxarea:=0;
assign(bnfile,fname);
reset(bnfile);
read(bnfile,dat); read(bnfile,dipdna); read (bnfile,thkness);
datamt:=int(dat);
for i:=1 to datamt do
begin
read(bnfile,arya[i]);
arya[i]:=arya[i]/dipdna;
if maxdna<arya[i] then maxdna:=arya[i];
read(bnfile,aryb[i]);
aryb[i]:=aryb[i]/(3.141593*sqr(thkness)/4);
naryb[i]:=aryb[i];
if maxarea<naryb[i] then maxarea:=naryb[i];
end;
close(bnfile);
end;
procedure redraw;
var
ratio: real;
begin
if ic<1000 then begin
gotoxy(1,1); write('Enter nth horizontal scaling factor:');
read(modif);
gotoxy(1,3); write('Enter nth reference sphere volume factor:');
read(modcrc);
end;
vri:=vri*modcrc;
graphcolormode;
colr:=1;
ratio:=0.02;
while ratio<1.02 do
begin ratio:=ratio+0.02;
setpt(ratio*ratio*ratio,sqr(ratio),right,left,top,bottom);
end;
ratio:=1;
while ratio<5 do
begin ratio:=ratio+0.02;
setpt((3*sqr(ratio)-1)/2,sqr(ratio),right,left,top,bottom);
end;
draw(0,0,0,199,1); draw(0,199,320,199,1);
end;
Procedure plotadj;
var
d,vcalc,acalc,at,vt,t,cutpt,cz,ct,v,area,r: real;
begin
t:=thkness; d:=exp(ln(t*t*t*vri)/3); r:=d/2; at:=pi*t*t/4; vt:=pi*t*t*t/6;
for i:=0 to 400 do
begin
cutpt:=i*(2*r+t)/400-r; cz:=cutpt-t; if cz<-r then cz:=-r;
ct:=cutpt; if ct>r then ct:=r;
v:=pi*((r*r*ct-ct*ct*ct/3)-(r*r*cz-cz*cz*cz/3));
vcalc:=v/vt;
```

-continued

PROGRAM RCM;

```
if abs(cz)<abs(ct) then area:=pi*(r*r-cz*cz) else area:=pi*(r*r-ct*ct);
if (ct>0) and (cz<0) then area:=pi*r*r;
acalc:=area/at; setpt(vcalc,acalc,top,bottom,right,left);
end;
colr:=2; factorx:=factorx*modif;
for i:=1 to datamt do
begin
setpt(arya[i]*factorx,naryb[i],right,left,top,bottom);
end;
gotoxy(1,5); write('DNA Index =',(vri/factorx):8:2);
gotoxy(1,1); write('                ');
gotoxy(1,1); write('Hit ENTER Key, or "q" to Quit');
read(ch);
end;
begin
GOTOXY(34,1); writeln('PROGRAM RCM');
GOTOXY(20,4);
WRITELN('Copyright (C) Jeffrey A. Freed, M.D. 1997');
gotoxy(30,6); writeln('All Rights Reserved');
gotoxy(10,8); writeln('This program embodies the
Reference Curve Method');
gotoxy(10,9); writeln('for correction of ploidy
measurements in tissue sections');
writeln('Enter data file name:'); read(fname);
increment:=0.1; factory:=1; factorx:=1; modif:=1;
readdata;
right:=maxdata*1.2;
left:=0;
top:=maxarea*1.2;
bottom:=0;
newthk:=thkness;
i:=1; modcrc:=1;
if maxarea>1 then factorx:=(3*maxarea-1)/(2*maxdna);
if maxarea<=1 then factorx:=exp(3*ln(maxarea)/2)/maxdna;
gotoxy(1,1); writeln('Press enter key to start');
graphcolormode;
ic:=1000; while ic>0 do
begin
redraw; plotadj; ic:=ic-1; if (ch='Q') or (ch='q') then
begin textmode; ic:=0; end; end;
END.
```

I claim:

1. A process of operating a general purpose data processor of known type to enable said data processor to calculate corrected quantitative microdensitometric deoxyribonucleic acid measurements in a tissue section of known section thickness, comprising the steps of:

(a) providing data means of inputting into a working memory of said data processor the integrated optical density datum and the area datum for each of a plurality of sectioned cell nuclei in said tissue section, and (b) providing parameter means of inputting into said working memory said known section thickness and the integrated optical density of an intact diploid nucleus, and (c) calculating an area datum ratio of said area datum to the area of a circle which has a diameter equal to said section thickness, for each of said plurality of sectioned cell nuclei, and (d) providing a drawing means of drawing a screen display of said data processor, comprising the steps of:

(1) providing a reference means of displaying a reference curve, comprising the steps of:

(i) providing calculating means of calculating a sphere section area and a sphere section volume of each of a plurality of sections of a reference sphere of predetermined diameter sectioned at said known section thickness and at various section positions including the central section, and (ii) calculating a sphere section volume ratio of each of said plurality of sections of said reference sphere by dividing each said sphere section volume by the volume of a sphere which has a diameter equal to said section thickness, and (iii) calculating a sphere section area ratio of each of said plurality of sections of said reference sphere by dividing each said sphere section area by the area of a circle which has a diameter equal to said section thickness, and (iv) plotting said sphere section volume ratio on said first axis against said sphere section area ratio on said second axis for each of said plurality of sections of said reference sphere, and (2) providing corresponding means of finding a corresponding reference curve, comprising the steps of:

(i) repeating said reference means using a new value of said predetermined diameter, and (ii) providing displaying means of displaying a scaled data curve comprising the steps of:

($\alpha$) obtaining a density product of said integrated optical density data and a scaling factor, and ($\beta$) plotting said density product on said first axis against said area data ratio on said second axis, and (iii) visually assessing the congruence of said scaled data curve and said reference curve, and (iv) repeating above steps (i) through (iii) until said scaled data curve coincides as nearly as possible with said reference curve, then designating said reference curve as said corresponding reference curve, and (f) calculating a corrected DNA index for said plurality of sectioned cell nuclei as the intact volume of said reference sphere of said corresponding reference curve divided by the product of the following three quantities: the volume of a sphere which has a diameter equal to said section thickness, said scaling factor, and said integrated optical density of an intact diploid nucleus, whereby the relationship existing between said sectioned cell nuclei and the corresponding intact nuclei which existed prior to the creation of said tissue section is demonstrated, and whereby said corrected DNA index is obtained.

2. The general purpose data processor of claim 1 wherein said data processor is a personal computer.

3. The integrated optical density data and the area data of claim 1 wherein said data are obtained by use of an image cytometer.

4. The integrated optical density data and the area data of claim 1 wherein said data are obtained by a computer simulation of corpuscle sectioning.

5. The data means of claim 1 wherein said data means consists of a disk drive, a data file, and a floppy disk containing said data file.

6. The data means of claim 1 wherein said data means consists of numerical keys, a keyboard containing said numerical keys, and a video monitor.

7. The parameter means of claim 1 wherein said parameter means consists of numerical keys, a keyboard containing said numerical keys, and a video monitor.

8. The calculating means of claim 1 wherein said calculating means comprises the steps of:

(a) centering said sphere at the origin of a three dimensional cartesian coordinate system, and (b) representing two sectioning planes as z=H and z=L, and (c) calculating said sphere section area as pi multiplied by the difference between the radius squared of said reference sphere and the square of the distance between center of said reference sphere and the closer of said two sectioning planes, and (d) calculating said sphere section volume as pi multiplied by $((R^2H-H^3/3)-(R^2L-L^3/3))$, where R is the radius of said sphere, H is the z coordinate of the top sectioning plane, and L is the z coordinate of the bottom sectioning plane.

9. The central section of claim 1 wherein said central section is the section which contains the center of said reference sphere midway between said sectioning planes.

10. The displaying means of claim 1 wherein said displaying means includes additionally displaying a plurality of points on a reference line which intersects the termini of all possible said reference curves.

* * * * *